(12) United States Patent
Alden et al.

(10) Patent No.: US 7,749,174 B2
(45) Date of Patent: Jul. 6, 2010

(54) METHOD AND APPARATUS FOR LANCET LAUNCHING DEVICE INTERGRATED ONTO A BLOOD-SAMPLING CARTRIDGE

(75) Inventors: Don Alden, Sunnyvale, CA (US); Dominique M. Freeman, La Honda, CA (US); Paul Lum, Los Altos, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 1012 days.

(21) Appl. No.: 10/363,510

(22) PCT Filed: Jun. 12, 2002

(86) PCT No.: PCT/US02/19060

§ 371 (c)(1),
(2), (4) Date: Sep. 29, 2003

(87) PCT Pub. No.: WO02/100254

PCT Pub. Date: Dec. 19, 2002

(65) Prior Publication Data

US 2005/0101981 A1     May 12, 2005

(51) Int. Cl.
*A61B 5/00* (2006.01)
(52) U.S. Cl. .................................. 600/583; 606/181
(58) Field of Classification Search ......... 606/181–183; 600/584, 556, 578, 583, 573
See application file for complete search history.

(56) References Cited

U.S. PATENT DOCUMENTS

| | | | |
|---|---|---|---|
| 1,733,847 A | 10/1929 | Wilmot | |
| 2,714,890 A | 8/1955 | Vang | 128/305 |
| 2,801,633 A | 8/1957 | Mauze, et al | |
| 3,086,288 A | 4/1963 | Balamuth et al. | 30/272 |
| 3,208,452 A | 9/1965 | Stern | 128/315 |
| 3,358,689 A | 12/1967 | Higgins | 128/329 |
| 3,494,358 A | 2/1970 | Grossenbacher | 128/218 |
| 3,626,929 A | 12/1971 | Sanz | 128/2 R |
| 3,673,475 A | 6/1972 | Britton, Jr. | 318/122 |
| 3,742,954 A | 7/1973 | Strickland | 128/302 |
| 3,832,776 A | 9/1974 | Sawyer | 30/272 |
| 3,953,172 A | 4/1976 | Shapiro | 23/230 |
| 4,077,406 A | 3/1978 | Sandhage et al. | 128/217 |
| 4,154,228 A | 5/1979 | Feldstein et al. | 128/329 |
| 4,203,446 A | 5/1980 | Höfert et al. | 128/329 |
| 4,223,674 A | 9/1980 | Fluent et al. | 128/217 |
| 4,224,125 A | 9/1980 | Nakamura | 204/195 B |
| 4,230,118 A | 10/1980 | Holman et al. | 128/314 |
| 4,340,669 A | 7/1982 | Bauer | 435/14 |

(Continued)

FOREIGN PATENT DOCUMENTS

DE        29824204        10/2000

(Continued)

*Primary Examiner*—Michael J Milano
*Assistant Examiner*—Victor X Nguyen
(74) *Attorney, Agent, or Firm*—Paul Davis; Goodwin Procter LLP

(57) ABSTRACT

A method and apparatus for obtaining a sample of blood. An embodiment consists of an apparatus which integrates lancing, sample collection, and analysis. The presence of patients finger on the active sampling area can be sensed by monitoring the pressure applied by the finger on the device.

8 Claims, 4 Drawing Sheets

U.S. PATENT DOCUMENTS

| | | | |
|---|---|---|---|
| 4,353,984 A | 10/1982 | Yamada | 435/14 |
| 4,356,826 A | 11/1982 | Kubota | 128/630 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,426,451 A | 1/1984 | Columbus | 436/518 |
| 4,426,884 A | 1/1984 | Polchaninoff | 73/172 |
| 4,449,529 A | 5/1984 | Burns et al. | 128/314 |
| 4,462,405 A | 7/1984 | Ehrlich | 128/329 |
| 4,469,110 A | 9/1984 | Slama | 128/770 |
| 4,517,978 A | 5/1985 | Levin | 128/314 |
| 4,518,384 A | 5/1985 | Tarello et al. | 604/61 |
| 4,535,773 A | 8/1985 | Yoon | 604/51 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,627,445 A * | 12/1986 | Garcia et al. | 600/583 |
| 4,637,403 A | 1/1987 | Garcia et al. | 128/770 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,653,513 A | 3/1987 | Dombrowski | 128/765 |
| 4,661,768 A | 4/1987 | Carusillo | |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,750,489 A | 6/1988 | Berkman et al. | 128/314 |
| 4,757,022 A | 7/1988 | Shults et al. | 435/291 |
| 4,787,398 A | 11/1988 | Garcia et al. | 128/770 |
| 4,794,926 A | 1/1989 | Munsch et al. | 606/183 |
| 4,814,142 A | 3/1989 | Gleisner | 422/56 |
| 4,814,661 A | 3/1989 | Ratzlaff | 310/328 |
| 4,820,010 A | 4/1989 | Scifres | 385/43 |
| 4,820,399 A | 4/1989 | Senda | 204/403 |
| 4,823,806 A | 4/1989 | Bajada | 128/744 |
| 4,824,639 A | 4/1989 | Hildenbrand | 422/56 |
| RE32,922 E | 5/1989 | Levin | 128/314 |
| 4,827,763 A | 5/1989 | Bourland | 73/172 |
| 4,830,959 A | 5/1989 | McNeil | 435/53 |
| 4,836,904 A | 6/1989 | Armstron | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birch | 204/409 |
| 4,911,794 A | 3/1990 | Parce | 204/1 T |
| 4,920,977 A | 5/1990 | Haynes | 128/770 |
| 4,924,879 A | 5/1990 | O'Brien | |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,995,402 A | 2/1991 | Smith et al. | 128/771 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,026,388 A | 6/1991 | Ingalz | 606/182 |
| 5,029,583 A | 7/1991 | Meserol | |
| 5,035,704 A | 7/1991 | Lambert et al. | 606/182 |
| 5,047,044 A | 9/1991 | Smith et al. | |
| 5,054,499 A | 10/1991 | Swierczek | 128/770 |
| 5,059,789 A | 10/1991 | Salcudean | 250/206.1 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,097,810 A | 3/1992 | Fishman et al. | 128/743 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,108,889 A | 4/1992 | Smith et al. | |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter et al. | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,145,565 A | 9/1992 | Kater et al. | 204/153.1 |
| 5,152,775 A | 10/1992 | Ruppert | 606/182 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,185,256 A | 2/1993 | Nankai | 435/174 |
| 5,187,100 A | 2/1993 | Matzinger | 436/16 |
| 5,188,118 A | 2/1993 | Terwilliger | 128/753 |
| 5,189,751 A | 3/1993 | Giuliani et al. | 15/22.1 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,217,480 A | 6/1993 | Haber | 606/182 |
| 5,222,504 A | 6/1993 | Solomon | 128/744 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,573 S | 12/1993 | Cerola | D24/147 |
| 5,272,087 A | 12/1993 | El Murr | 435/291 |
| 5,279,294 A | 1/1994 | Anderson et al. | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollmann | 435/288 |
| 5,304,192 A | 4/1994 | Crouse | 606/181 |

| Patent No. | Date | Inventor | Class |
|---|---|---|---|
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,316,012 A | 5/1994 | Siegal | 128/744 |
| 5,318,583 A | 6/1994 | Rabenau | 606/182 |
| 5,320,607 A | 6/1994 | Ishibashi | 604/115 |
| 5,320,808 A | 6/1994 | Holen et al. | 422/64 |
| 5,324,302 A | 6/1994 | Crouse | 606/181 |
| 5,324,303 A | 6/1994 | Strong | 606/181 |
| 5,332,479 A | 7/1994 | Uenoyama | 204/153.12 |
| 5,350,392 A | 9/1994 | Purcell | 606/182 |
| 5,354,287 A | 10/1994 | Wacks | 604/232 |
| 5,354,447 A | 10/1994 | Uenoyama | 204/403 |
| 5,356,420 A | 10/1994 | Czernecki | 606/182 |
| 5,360,410 A | 11/1994 | Wacks | 604/232 |
| 5,366,469 A | 11/1994 | Steg | 606/182 |
| 5,366,470 A | 11/1994 | Ramel | 606/183 |
| 5,366,609 A | 11/1994 | White | 204/403 |
| 5,368,047 A | 11/1994 | Suzuki et al. | 128/765 |
| 5,375,397 A | 12/1994 | Ferrand | 54/66 |
| 5,378,628 A | 1/1995 | Graetzel | 435/288 |
| 5,382,346 A | 1/1995 | Uenoyama | 204/403 |
| 5,383,885 A | 1/1995 | Bland | 606/182 |
| 5,389,534 A | 2/1995 | Gentezkow | 435/180 |
| 5,393,903 A | 2/1995 | Graetzel | 556/137 |
| 5,395,387 A | 3/1995 | Burns | 606/181 |
| 5,397,334 A | 3/1995 | Schenk | 606/182 |
| 5,401,376 A | 3/1995 | Foos | 204/415 |
| 5,402,798 A | 4/1995 | Swierczek | 128/770 |
| 5,407,545 A | 4/1995 | Hirose | 204/153.12 |
| 5,407,554 A | 4/1995 | Saurer | 204/403 |
| 5,407,818 A | 4/1995 | Gentezkow | 435/180 |
| 5,409,583 A | 4/1995 | Yoshioka | 204/153.12 |
| 5,409,664 A | 4/1995 | Allen | |
| 5,410,059 A | 4/1995 | Fraser | 546/10 |
| 5,415,169 A | 5/1995 | Siczek et al. | 128/653.1 |
| 5,423,847 A | 6/1995 | Strong et al. | 606/182 |
| 5,436,161 A | 7/1995 | Bergstrom | 435/291 |
| 5,437,999 A | 8/1995 | Diebold | 435/288 |
| 5,443,701 A | 8/1995 | Willner | 204/153 |
| 5,445,920 A | 8/1995 | Saito | 430/311 |
| D362,719 S | 9/1995 | Kaplan | D24/147 |
| 5,454,828 A | 10/1995 | Schraga | 606/182 |
| 5,456,875 A | 10/1995 | Lambert | 264/328.1 |
| 5,464,418 A | 11/1995 | Schraga | 606/182 |
| 5,471,102 A | 11/1995 | Becker | 310/50 |
| 5,472,427 A | 12/1995 | Rammler | 604/164 |
| 5,474,084 A | 12/1995 | Cunniff | 128/744 |
| 5,476,474 A | 12/1995 | Davis | 606/182 |
| 5,480,387 A | 1/1996 | Gabriel | 604/134 |
| 5,487,748 A | 1/1996 | Marshall | 606/182 |
| 5,496,453 A | 3/1996 | Uenoyama | 205/777.5 |
| 5,498,542 A | 3/1996 | Corey | 435/283.1 |
| 5,509,410 A | 4/1996 | Hill | 128/637 |
| 5,510,266 A | 4/1996 | Bonner et al. | 436/43 |
| 5,512,159 A | 4/1996 | Yoshioka | 204/403 |
| 5,514,152 A | 5/1996 | Smith et al. | |
| 5,518,006 A | 5/1996 | Mawhirt | 128/770 |
| 5,524,636 A | 6/1996 | Sarvazyan | 128/774 |
| 5,525,511 A | 6/1996 | D'Costa | 435/287.9 |
| 5,527,333 A | 6/1996 | Nikkels | 606/182 |
| 5,527,334 A | 6/1996 | Kanner | 606/182 |
| 5,529,074 A | 6/1996 | Greenfield | 128/744 |
| 5,540,709 A | 7/1996 | Ramel | 606/183 |
| 5,543,326 A | 8/1996 | Heller | 435/287.9 |
| 5,545,174 A | 8/1996 | Schenk | 606/182 |
| 5,547,702 A | 8/1996 | Gleisner | 427/2.13 |
| 5,554,166 A | 9/1996 | Lange | 606/182 |
| 5,558,834 A | 9/1996 | Chu | 422/55 |
| 5,569,286 A | 10/1996 | Peckham | 606/181 |
| 5,569,287 A | 10/1996 | Tezuka | 606/182 |
| 5,571,132 A | 11/1996 | Mawhirt | 606/182 |
| 5,575,403 A | 11/1996 | Charlton et al. | 221/31 |
| 5,575,895 A | 11/1996 | Ikeda | 204/403 |
| 5,582,697 A | 12/1996 | Ikeda | 204/403 |
| 5,584,846 A | 12/1996 | Mawhirt | 606/181 |
| 5,593,852 A | 1/1997 | Heller | 435/14 |
| 5,609,749 A | 3/1997 | Yamauchi | 205/777.5 |
| 5,613,978 A | 3/1997 | Harding | 606/181 |
| 5,620,579 A | 4/1997 | Genshaw | 204/402 |
| 5,624,537 A | 4/1997 | Turner | 204/403 |
| D379,516 S | 5/1997 | Rutter | D24/146 |
| 5,628,764 A | 5/1997 | Schraga | 606/182 |
| 5,628,765 A | 5/1997 | Morita | 606/182 |
| 5,628,890 A | 5/1997 | Carter | 204/403 |
| 5,630,986 A | 5/1997 | Charlton et al. | 422/64 |
| 5,632,410 A | 5/1997 | Moulton et al. | 221/79 |
| 5,643,306 A | 7/1997 | Schraga | 606/182 |
| 5,645,555 A | 7/1997 | Davis | 606/182 |
| 5,650,062 A | 7/1997 | Ikeda | 205/778 |
| 5,653,863 A | 8/1997 | Genshaw | 205/777.5 |
| 5,657,760 A | 8/1997 | Ying et al. | 128/660.03 |
| 5,658,444 A | 8/1997 | Black | 204/415 |
| 5,662,127 A | 9/1997 | De Vaughn | 128/765 |
| 5,662,672 A | 9/1997 | Pambianchi | 606/181 |
| 5,680,872 A | 10/1997 | Sesekura | 128/760 |
| 5,682,884 A | 11/1997 | Hill | 128/637 |
| 5,683,562 A | 11/1997 | Schaffar | 204/403 |
| 5,695,947 A | 12/1997 | Guo | 435/11 |
| 5,700,695 A | 12/1997 | Yassinzadeh | 436/180 |
| 5,705,045 A | 1/1998 | Park | 204/403 |
| 5,708,247 A | 1/1998 | McAleer | 204/403 |
| 5,709,668 A | 1/1998 | Wacks | 604/232 |
| 5,710,011 A | 1/1998 | Forrow | 435/25 |
| 5,714,390 A | 2/1998 | Hallowitz et al. | 436/526 |
| 5,720,862 A | 2/1998 | Hamamoto | 204/403 |
| 5,720,924 A | 2/1998 | Eikmeier | 422/102 |
| D392,391 S | 3/1998 | Douglas | D24/225 |
| 5,723,284 A | 3/1998 | Ye | 435/4 |
| 5,727,548 A | 3/1998 | Hill | 128/637 |
| 5,730,753 A | 3/1998 | Morita | 606/181 |
| 5,733,300 A | 3/1998 | Pambianchi | 606/181 |
| D393,716 S | 4/1998 | Brenneman | D24/147 |
| D393,717 S | 4/1998 | Brenneman | D24/147 |
| 5,738,244 A | 4/1998 | Charlton et al. | 221/26 |
| 5,741,634 A | 4/1998 | Nozoe | 435/4 |
| RE35,803 E | 5/1998 | Lange | 606/182 |
| 5,746,217 A | 5/1998 | Erickson | 128/760 |
| 5,755,733 A | 5/1998 | Morita | 606/182 |
| 5,758,643 A | 6/1998 | Wong et al. | 128/632 |
| 5,759,364 A | 6/1998 | Charlton | 204/403 |
| 5,762,770 A | 6/1998 | Pritchard | 204/403 |
| 5,770,086 A | 6/1998 | Indriksons et al. | |
| 5,770,369 A | 6/1998 | Meade | 435/6 |
| 5,772,586 A | 6/1998 | Heinonen | 600/300 |
| 5,772,677 A | 6/1998 | Mawhirt | 606/181 |
| 5,773,270 A | 6/1998 | D'Orazio | 435/177 |
| 5,776,157 A | 7/1998 | Thorne et al. | 606/182 |
| 5,776,719 A | 7/1998 | Douglas | 435/28 |
| 5,782,770 A | 7/1998 | Mooradian | 600/476 |
| 5,782,852 A | 7/1998 | Foggia | 606/182 |
| 5,788,651 A | 8/1998 | Weilandt | 600/567 |
| 5,788,652 A | 8/1998 | Rahn | 600/577 |
| 5,795,725 A | 8/1998 | Buechler | 435/7.1 |
| 5,795,774 A | 8/1998 | Matsumoto | 435/287.9 |
| 5,797,940 A | 8/1998 | Mawhirt | 606/167 |
| 5,797,942 A | 8/1998 | Schraga | 606/182 |
| 5,798,030 A | 8/1998 | Raguse | 204/403 |
| 5,798,031 A | 8/1998 | Charlton | 204/403 |
| 5,800,781 A | 9/1998 | Gavin et al. | 422/73 |
| 5,801,057 A | 9/1998 | Smart | 436/68 |
| 5,810,199 A | 9/1998 | Charlton et al. | 221/31 |
| 5,820,551 A | 10/1998 | Hill | 600/347 |
| 5,823,973 A | 10/1998 | Racchini et al. | 600/573 |
| 5,824,491 A | 10/1998 | Priest | 435/28 |

| | | | | | | | |
|---|---|---|---|---|---|---|---|
| 5,830,219 | A | 11/1998 | Bird et al. .................... 606/130 | 6,071,251 | A | 6/2000 | Cunningham ............... 600/584 |
| 5,840,020 | A | 11/1998 | Heinonen .................... 600/309 | 6,071,294 | A | 6/2000 | Simons et al. .............. 606/181 |
| 5,840,171 | A | 11/1998 | Birch ........................ 205/335 | 6,074,360 | A | 6/2000 | Haar et al. .................... 604/57 |
| 5,846,490 | A | 12/1998 | Yokota et al. ................. 422/66 | 6,077,408 | A | 6/2000 | Miyamoto .................... 204/403 |
| 5,849,174 | A | 12/1998 | Sanghera .................... 205/775 | 6,080,172 | A | 6/2000 | Fujiwara .................... 606/166 |
| 5,854,074 | A | 12/1998 | Charlton et al. ............... 436/46 | 6,083,710 | A | 7/2000 | Heller .......................... 435/14 |
| D403,975 | S | 1/1999 | Douglas ...................... D10/81 | 6,086,562 | A | 7/2000 | Jacobsen .................... 604/156 |
| 5,855,801 | A | 1/1999 | Lin et al. ........................ 216/2 | 6,090,078 | A | 7/2000 | Erskine .................... 604/198 |
| 5,857,983 | A | 1/1999 | Douglas ...................... 600/538 | 6,093,156 | A | 7/2000 | Cunningham |
| 5,860,922 | A | 1/1999 | Gordon et al. ............... 600/431 | 6,103,033 | A | 8/2000 | Say .......................... 156/73.1 |
| 5,863,800 | A | 1/1999 | Eikmeier et al. ............... 436/48 | 6,107,083 | A | 8/2000 | Collins ........................ 435/288 |
| 5,866,353 | A | 2/1999 | Berneth ........................ 435/26 | 6,117,630 | A | 9/2000 | Reber et al. .................... 435/4 |
| 5,868,772 | A | 2/1999 | LeVaughn .................... 606/181 | 6,120,462 | A | 9/2000 | Hibner et al. ............... 600/566 |
| 5,869,972 | A | 2/1999 | Birch ........................ 324/439 | 6,120,676 | A | 9/2000 | Heller .................... 205/777.5 |
| 5,871,494 | A | 2/1999 | Simons et al. | 6,121,009 | A | 9/2000 | Heller .......................... 435/14 |
| 5,872,713 | A | 2/1999 | Douglas ........................ 702/85 | 6,129,823 | A | 10/2000 | Hughes .................... 204/403.01 |
| 5,873,887 | A | 2/1999 | King .......................... 606/182 | 6,132,449 | A | 10/2000 | Lum et al. .................... 606/181 |
| 5,876,957 | A | 3/1999 | Douglas ........................ 435/28 | 6,133,837 | A | 10/2000 | Riley ........................ 340/573.1 |
| 5,879,311 | A | 3/1999 | Duchon et al. ............... 600/583 | 6,134,461 | A | 10/2000 | Say .......................... 600/345 |
| 5,879,373 | A | 3/1999 | Roeper ........................ 606/344 | 6,136,013 | A | 10/2000 | Marshall et al. ............... 606/167 |
| 5,880,829 | A | 3/1999 | Kauhaniemi et al. ........ 356/246 | 6,139,562 | A | 10/2000 | Mauze et al. ............... 606/171 |
| 5,882,494 | A | 3/1999 | van Antwerp ............... 204/403 | 6,143,164 | A | 11/2000 | Heller et al. .............. 205/777.5 |
| 5,885,211 | A | 3/1999 | Eppstein et al. ............. 600/309 | 6,152,942 | A | 11/2000 | Brenneman et al. ......... 606/181 |
| 5,891,053 | A | 4/1999 | Sesekura .................... 600/583 | 6,153,069 | A | 11/2000 | Pottgen .................... 204/403 |
| 5,899,915 | A | 5/1999 | Saadat et al. | RE36,991 | E | 12/2000 | Yamamoto .................... 204/403 |
| 5,900,130 | A | 5/1999 | Benvegnu .................... 204/453 | 6,155,992 | A | 12/2000 | Henning et al. ............... 600/583 |
| 5,906,921 | A | 5/1999 | Ikeda .......................... 435/25 | 6,156,051 | A | 12/2000 | Schraga .................... 606/181 |
| D411,619 | S | 6/1999 | Duchon ...................... D24/146 | 6,157,442 | A | 12/2000 | Raskas ........................ 356/39 |
| 5,916,156 | A | 6/1999 | Hildenbrand ............... 600/347 | 6,159,424 | A | 12/2000 | Kauhaniemi et al. .......... 422/63 |
| 5,916,229 | A | 6/1999 | Evans ........................ 606/171 | 6,162,611 | A | 12/2000 | Heller ........................ 435/14 |
| 5,916,230 | A | 6/1999 | Brenneman ................. 606/172 | 6,171,325 | B1 | 1/2001 | Mauze et al. ............... 606/171 |
| 5,921,963 | A | 7/1999 | Erez ........................ 604/192 | 6,175,752 | B1 | 1/2001 | Say .......................... 600/345 |
| 5,922,188 | A | 7/1999 | Ikeda .................... 204/777.5 | 6,176,865 | B1 | 1/2001 | Mauze et al. ............... 606/171 |
| RE36,268 | E | 8/1999 | Szuminsky .............. 205/777.5 | 6,177,000 | B1 | 1/2001 | Peterson .................. 205/777.5 |
| 5,935,075 | A | 8/1999 | Casscells et al. ............. 600/474 | 6,177,931 | B1 | 1/2001 | Alexander et al. |
| 5,938,679 | A | 8/1999 | Freeman et al. ............. 606/181 | 6,183,489 | B1 | 2/2001 | Douglas et al. .............. 606/181 |
| 5,940,153 | A | 8/1999 | Castaneda | 6,190,612 | B1 | 2/2001 | Berger ........................ 422/82.07 |
| 5,951,492 | A | 9/1999 | Douglas .................... 600/583 | 6,191,852 | B1 | 2/2001 | Paffhausen ................. 356/244 |
| 5,951,493 | A | 9/1999 | Douglas et al. ............. 600/583 | 6,192,891 | B1 | 2/2001 | Gravel ........................ 128/920 |
| 5,951,582 | A | 9/1999 | Thorne et al. ............... 606/182 | 6,193,673 | B1 | 2/2001 | Viola et al. ................. 600/568 |
| 5,951,836 | A | 9/1999 | McAleer .................... 204/403 | 6,194,900 | B1 | 2/2001 | Freeman .................... 324/321 |
| 5,954,738 | A | 9/1999 | LeVaughn .................... 606/181 | 6,197,257 | B1 | 3/2001 | Raskas .................... 422/82.05 |
| 5,958,199 | A | 9/1999 | Miyamoto .................... 204/403 | 6,203,504 | B1 | 3/2001 | Latterell et al. ............. 600/576 |
| 5,965,380 | A | 10/1999 | Heller .......................... 435/14 | 6,206,841 | B1 | 3/2001 | Cunningham et al. ........ 600/584 |
| 5,968,063 | A | 10/1999 | Chu et al. .................... 606/185 | 6,210,420 | B1 | 4/2001 | Mauze et al. ............... 606/182 |
| 5,971,941 | A | 10/1999 | Simons et al. ............... 600/573 | 6,210,421 | B1 | 4/2001 | Böcker et al. ............... 606/182 |
| 5,972,199 | A | 10/1999 | Heller .................... 205/777.5 | 6,212,417 | B1 | 4/2001 | Ikeda .................... 204/403.14 |
| 5,983,193 | A | 11/1999 | Heinonen ...................... 705/2 | 6,214,804 | B1 | 4/2001 | Felgner ........................ 514/44 |
| 5,985,116 | A | 11/1999 | Ikeda ........................ 204/403 | 6,221,023 | B1 * | 4/2001 | Matsuba et al. ............. 600/486 |
| 5,993,400 | A | 11/1999 | Rincoe ........................ 600/595 | 6,221,238 | B1 | 4/2001 | Grundig .................... 205/777.5 |
| 5,993,434 | A * | 11/1999 | Dev et al. .................... 604/501 | 6,225,078 | B1 | 5/2001 | Ikeda .......................... 435/25 |
| 5,997,561 | A | 12/1999 | Boecker .................... 606/182 | 6,228,100 | B1 | 5/2001 | Schraga |
| 5,997,817 | A | 12/1999 | Crismore .................... 422/58 | 6,230,501 | B1 | 5/2001 | Bailey ........................ 62/51.1 |
| 5,997,818 | A | 12/1999 | Hacker ........................ 422/681 | 6,231,531 | B1 | 5/2001 | Lum et al. .................... 601/46 |
| 6,001,067 | A | 12/1999 | Shults ........................ 600/584 | 6,241,862 | B1 | 6/2001 | McAleer .................... 204/403 |
| 6,020,110 | A | 2/2000 | Williams .................... 430/315 | 6,245,060 | B1 | 6/2001 | Loomis ........................ 606/9 |
| 6,022,324 | A | 2/2000 | Skinner .................... 600/566 | 6,251,260 | B1 | 6/2001 | Heller .................... 205/777.5 |
| 6,022,366 | A | 2/2000 | Schraga .................... 606/181 | 6,254,831 | B1 | 7/2001 | Barnard .................... 422/82.08 |
| 6,027,459 | A | 2/2000 | Shain et al. ................. 600/573 | 6,256,533 | B1 | 7/2001 | Vuzhakov .................... 604/21 |
| 6,030,399 | A | 2/2000 | Ignotz ........................ 606/167 | 6,258,229 | B1 | 7/2001 | Winarta .................... 204/403 |
| 6,030,827 | A | 2/2000 | Davis ........................ 435/287 | 6,258,254 | B1 | 7/2001 | Miyamoto .................... 205/777.5 |
| 6,033,421 | A | 3/2000 | Theiss ........................ 606/186 | 6,261,241 | B1 | 7/2001 | Burbank et al. ............. 600/564 |
| 6,033,866 | A | 3/2000 | Guo ............................ 435/14 | 6,261,245 | B1 | 7/2001 | Kawai et al. ................. 600/576 |
| 6,036,924 | A | 3/2000 | Simons et al. ............... 422/100 | 6,261,519 | B1 | 7/2001 | Harding |
| 6,048,352 | A | 4/2000 | Douglas et al. ............. 606/181 | 6,268,161 | B1 | 7/2001 | Han ............................ 435/14 |
| D424,696 | S | 5/2000 | Ray .......................... D24/169 | 6,270,637 | B1 | 8/2001 | Crismore .................... 204/403 |
| 6,060,327 | A | 5/2000 | Keen ........................ 436/518 | 6,272,359 | B1 | 8/2001 | Kivela .................... 455/567 |
| 6,063,039 | A | 5/2000 | Cunningham ............... 600/573 | 6,281,006 | B1 | 8/2001 | Heller .................... 435/287.9 |
| 6,066,296 | A | 5/2000 | Brady ........................ 422/63 | 6,283,926 | B1 | 9/2001 | Cunningham et al. ........ 600/573 |
| 6,067,463 | A | 5/2000 | Jeng ........................ 600/336 | 6,283,982 | B1 | 9/2001 | Levaughn .................... 606/172 |
| D426,638 | S | 6/2000 | Ray .......................... D24/169 | 6,284,478 | B1 | 9/2001 | Heller .......................... 435/14 |
| 6,071,249 | A | 6/2000 | Cunningham ............... 600/578 | 6,285,448 | B1 | 9/2001 | Kuenstner .................... 356/39 |
| 6,071,250 | A | 6/2000 | Douglas .................... 600/583 | 6,285,454 | B1 | 9/2001 | Douglas et al. ............. 356/446 |

| Patent | Date | Inventor | Class |
|---|---|---|---|
| 6,290,683 B1 | 9/2001 | Erez | 604/273 |
| 6,295,506 B1 | 9/2001 | Heinonen | 702/104 |
| 6,299,757 B1 | 10/2001 | Feldman | 205/775 |
| 6,302,855 B1 | 10/2001 | Lav | 600/584 |
| 6,306,104 B1 | 10/2001 | Cunningham et al. | 600/573 |
| 6,306,152 B1 | 10/2001 | Verdonk et al. | 606/182 |
| 6,306,347 B1 | 10/2001 | Mason | 422/58 |
| 6,309,535 B1 | 10/2001 | Williams | 205/777.5 |
| 6,312,612 B1 | 11/2001 | Sherman | 216/2 |
| 6,315,738 B1 | 11/2001 | Nishikawa | |
| 6,319,210 B1 | 11/2001 | Douglas et al. | 600/583 |
| 6,322,574 B1 | 11/2001 | Lloyd | 606/181 |
| 6,331,163 B1 | 12/2001 | Kaplan | 600/486 |
| 6,332,871 B1 * | 12/2001 | Douglas et al. | 600/583 |
| 6,334,363 B1 | 1/2002 | Testud | 73/862 |
| 6,334,856 B1 | 1/2002 | Allen | 604/191 |
| 6,338,790 B1 | 1/2002 | Feldman | 205/777.5 |
| 6,350,273 B1 | 2/2002 | Minagawa | 606/186 |
| 6,350,451 B1 | 2/2002 | Horn | 424/184.1 |
| 6,352,514 B1 | 3/2002 | Douglas et al. | 600/583 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,364,890 B1 | 4/2002 | Lum et al. | 606/181 |
| 6,375,627 B1 | 4/2002 | Mauze et al. | 600/584 |
| 6,379,301 B1 | 4/2002 | Worthington | 600/309 |
| 6,379,317 B1 | 4/2002 | Kintzig et al. | 600/573 |
| 6,379,324 B1 | 4/2002 | Gartstein | 604/22 |
| 6,379,969 B1 | 4/2002 | Mauze et al. | 436/68 |
| 6,387,709 B1 | 5/2002 | Mason | 436/164 |
| 6,391,005 B1 | 5/2002 | Lum et al. | 604/117 |
| 6,399,394 B1 | 6/2002 | Dahm | 436/180 |
| 6,402,701 B1 | 6/2002 | Kaplan et al. | 600/567 |
| 6,402,704 B1 | 6/2002 | McMorrow | 600/576 |
| 6,409,740 B1 | 6/2002 | Kuhr et al. | 606/182 |
| 6,413,410 B1 | 7/2002 | Hodges | 205/775 |
| 6,413,411 B1 | 7/2002 | Pottgen | 205/777.5 |
| 6,421,633 B1 | 7/2002 | Heinonen | 703/11 |
| 6,423,014 B1 | 7/2002 | Churchill et al. | |
| 6,428,664 B1 | 8/2002 | Bhullar | 204/403.03 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,451,040 B1 | 9/2002 | Purcell | 606/181 |
| 6,458,258 B2 | 10/2002 | Taniike | 204/403 |
| 6,461,496 B1 | 10/2002 | Feldman et al. | 205/777.5 |
| 6,462,162 B2 | 10/2002 | van Antwerp | 528/77 |
| 6,471,903 B2 | 10/2002 | Sherman | 264/328.1 |
| 6,472,220 B1 | 10/2002 | Simons et al. | 436/63 |
| 6,475,436 B1 | 11/2002 | Schabbach | 422/64 |
| 6,475,750 B1 | 11/2002 | Han | 435/14 |
| 6,484,046 B1 | 11/2002 | Say | 600/345 |
| 6,485,439 B1 | 11/2002 | Roe et al. | 600/578 |
| 6,488,891 B2 | 12/2002 | Mason et al. | 422/58 |
| 6,491,709 B2 | 12/2002 | Sharma et al. | 606/181 |
| 6,497,845 B1 | 12/2002 | Sacherer | 422/104 |
| 6,501,404 B2 | 12/2002 | Walker | 341/143 |
| 6,503,210 B1 | 1/2003 | Hirao et al. | 600/576 |
| 6,503,231 B1 | 1/2003 | Prausnitz | 604/272 |
| 6,506,168 B1 | 1/2003 | Fathallah | 600/578 |
| 6,506,575 B1 | 1/2003 | Knappe et al. | 435/25 |
| 6,508,795 B1 | 1/2003 | Samuelsson | 604/113 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | 600/583 |
| 6,530,937 B1 | 3/2003 | Schraga | 606/182 |
| 6,533,949 B1 | 3/2003 | Yeshurun | 216/11 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller et al. | 205/777.5 |
| 6,555,061 B1 | 4/2003 | Leong | 422/58 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,561,989 B2 | 5/2003 | Whitson | 600/573 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,576,101 B1 | 6/2003 | Heller | 204/403.14 |
| 6,576,416 B2 | 6/2003 | Haviland | 435/4 |
| 6,579,690 B1 | 6/2003 | Bonnecaze et al. | 435/14 |
| 6,584,338 B1 * | 6/2003 | Van Muiswinkel | 600/419 |
| 6,587,705 B1 | 7/2003 | Berner et al. | 600/347 |
| 6,589,260 B1 | 7/2003 | Schmelzeisen-Redeker | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,641,533 B2 | 11/2003 | Causey | 600/300 |
| 6,645,368 B1 | 11/2003 | Beatty | 205/792 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Petersson | 600/316 |
| 6,679,841 B2 | 1/2004 | Bojan | 600/309 |
| 6,679,852 B1 | 1/2004 | Forster et al. | 600/583 |
| 6,706,000 B2 | 3/2004 | Perez | 600/583 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Nakaminami | 204/403.14 |
| 6,743,211 B1 | 6/2004 | Prausnitz | 604/239 |
| 6,749,792 B2 | 6/2004 | Olson | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |

| Patent No. | Date | Inventor | Class |
|---|---|---|---|
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Nakaminami et al. | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 * | 9/2004 | Douglas et al. | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grubge | |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,847,451 B2 | 1/2005 | Pugh | 356/436 |
| 6,849,052 B2 | 2/2005 | Uchigaki | 600/584 |
| 6,849,168 B2 | 2/2005 | Madou | 204/416 |
| 6,849,216 B2 | 2/2005 | Rappin | 264/134 |
| 6,850,790 B2 | 2/2005 | Berner | 600/347 |
| 6,881,541 B2 | 4/2005 | Petersen et al. | |
| 6,918,901 B1 | 7/2005 | Theeuwes et al. | |
| 6,982,431 B2 | 1/2006 | Modlin et al. | |
| 7,160,678 B1 | 1/2007 | Kayyem et al. | |
| 7,225,535 B2 | 6/2007 | Feldman et al. | |
| 7,226,461 B2 | 6/2007 | Boecker et al. | |
| 2001/0017269 A1 | 8/2001 | Heller | 205/777.5 |
| 2001/0027328 A1 | 10/2001 | Lum | 606/186 |
| 2001/0031931 A1 | 10/2001 | Cunningham et al. | 600/573 |
| 2001/0054319 A1 | 12/2001 | Heller | 73/849 |
| 2002/0002344 A1 | 1/2002 | Douglas et al. | 600/583 |
| 2002/0004196 A1 | 1/2002 | Whitson | 435/4 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum et al. | |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081588 A1 | 6/2002 | De Lumley-Woodyear | 435/6 |
| 2002/0082543 A1 | 6/2002 | Park et al. | 604/21 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan et al. | |
| 2002/0103499 A1 | 8/2002 | Perez et al. | 606/182 |
| 2002/0120216 A1 | 8/2002 | Fritz | 600/583 |
| 2002/0130042 A1 | 9/2002 | Moerman | 204/403.01 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028126 A1 | 2/2003 | List | 600/583 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 600/576 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman et al. | 606/181 |
| 2003/0083686 A1 | 5/2003 | Freeman | 606/181 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti | 702/31 |
| 2003/0136189 A1 | 7/2003 | Lauman et al. | |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |

| Pub. No. | Date | Name | Class |
|---|---|---|---|
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | Yuzhakov et al. | 600/584 |
| 2003/0212347 A1 | 11/2003 | Sohrab | 600/584 |
| 2003/0212423 A1 | 11/2003 | Pugh | 606/181 |
| 2003/0212424 A1 | 11/2003 | Briggs | 606/181 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0026243 A1 | 2/2004 | Davies | 204/403.14 |
| 2004/0030353 A1 | 2/2004 | Schmelzeisen-Redeker | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0256228 A1 | 2/2004 | Huang | 204/434 |
| 2004/0049220 A1 | 3/2004 | Boecker | 606/181 |
| 2004/0054267 A1 | 3/2004 | Feldman | 600/316 |
| 2004/0055898 A1 | 3/2004 | Heller | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0092995 A1 | 5/2004 | Boecker | 606/181 |
| 2004/0096991 A1 | 5/2004 | Zhang | 436/518 |
| 2004/0098010 A1 | 5/2004 | Davison | 606/181 |
| 2004/0102803 A1 | 5/2004 | Boecker | 606/183 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0115754 A1 | 6/2004 | Chang | 435/14 |
| 2004/0115831 A1 | 6/2004 | Meathrel | 436/514 |
| 2004/0116829 A1 | 6/2004 | Raney | 600/573 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Kheiri | 606/182 |
| 2004/0167383 A1 | 8/2004 | Kim | 600/365 |
| 2004/0171057 A1 | 9/2004 | Mauze et al. | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0194302 A1 | 10/2004 | Bhullar | 29/847 |
| 2004/0197301 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0200720 A1 | 10/2004 | Musho | 204/403.01 |
| 2004/0200721 A1 | 10/2004 | Bhullar | 204/403.01 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.11 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Schraga | 606/181 |
| 2004/0238357 A1 | 12/2004 | Bhullar | 204/400 |

| | | | | | |
|---|---|---|---|---|---|
| 2004/0238358 A1 | 12/2004 | Forrow et al. ............... 204/403 | EP | 0374355 | 6/1993 |
| 2004/0238359 A1 | 12/2004 | Ikeda .................... 204/403.1 | EP | 0351891 | 9/1993 |
| 2004/0241746 A1 | 12/2004 | Adlassnig ................ 435/7.1 | EP | 0593096 | 4/1994 |
| 2004/0242977 A1 | 12/2004 | Dosmann ................... 600/315 | EP | 0415388 | 5/1995 |
| 2004/0243164 A1 | 12/2004 | D'Agostino ............... 606/181 | EP | 0505494 | 7/1995 |
| 2004/0243165 A1 | 12/2004 | Koike ..................... 606/181 | EP | 0359831 | 8/1995 |
| 2004/0245101 A1 | 12/2004 | Willner .................... 204/403 | EP | 0471986 | 10/1995 |
| 2004/0248282 A1 | 12/2004 | Sobha .................. 435/287.2 | EP | 0368474 | 12/1995 |
| 2004/0248312 A1 | 12/2004 | Vreeke ..................... 436/95 | EP | 0461601 | 12/1995 |
| 2004/0249310 A1 | 12/2004 | Shartle ..................... 600/583 | EP | 0429076 | 1/1996 |
| 2004/0249311 A1 | 12/2004 | Haar ........................ 600/584 | EP | 0552223 | 7/1996 |
| 2004/0249405 A1 | 12/2004 | Watanabe ................. 606/181 | EP | 0735363 | 10/1996 |
| 2004/0249406 A1 | 12/2004 | Griffin ..................... 606/182 | EP | 0505504 | 3/1997 |
| 2004/0251131 A1 | 12/2004 | Ueno ....................... 204/403 | EP | 0406304 | 8/1997 |
| 2004/0253634 A1 | 12/2004 | Wang ...................... 435/7.1 | EP | 0537761 | 8/1997 |
| 2004/0254434 A1 | 12/2004 | Goodnow ................. 600/365 | EP | 0795601 | 9/1997 |
| 2004/0254599 A1 | 12/2004 | Lipoma ..................... 606/181 | EP | 0562370 | 11/1997 |
| 2004/0256248 A1 | 12/2004 | Burke ....................... 205/792 | EP | 0415393 | 12/1997 |
| 2004/0256685 A1 | 12/2004 | Chou ........................ 257/414 | EP | 0560336 | 5/1998 |
| 2004/0258564 A1 | 12/2004 | Charlton ..................... 422/58 | EP | 0878 708 | 11/1998 |
| 2004/0260204 A1 | 12/2004 | Boecker .................... 600/584 | EP | 0 898 936 A2 | 3/1999 |
| 2004/0260324 A1 | 12/2004 | Fukuzawa ................. 606/181 | EP | 0505475 | 3/1999 |
| 2004/0260325 A1 | 12/2004 | Kuhr ....................... 606/181 | EP | 0901018 | 3/1999 |
| 2004/0260326 A1 | 12/2004 | Lipoma ................... 606/182 | EP | 0470649 | 6/1999 |
| 2004/0260511 A1 | 12/2004 | Burke ....................... 702/182 | EP | 0 951 939 | 10/1999 |
| 2004/0267105 A1 | 12/2004 | Monfre ..................... 600/344 | EP | 0 951 939 A2 | 10/1999 |
| 2004/0267160 A9 | 12/2004 | Perez ....................... 600/583 | EP | 0847447 | 11/1999 |
| 2004/0267229 A1 | 12/2004 | Moerman ................. 604/500 | EP | 0964059 | 12/1999 |
| 2004/0267299 A1 | 12/2004 | Kuriger ...................... 606/181 | EP | 0969097 | 1/2000 |
| 2004/0267300 A1 | 12/2004 | Mace ....................... 606/182 | EP | 0 985 376 | 5/2000 |
| 2005/0000806 A1 | 1/2005 | Hsieh ...................... 203/403.1 | EP | 1021950 | 7/2000 |
| 2005/0000807 A1 | 1/2005 | Wang ..................... 204/403.81 | EP | 0894869 | 2/2001 |
| 2005/0000808 A1 | 1/2005 | Cui ...................... 203/403.14 | EP | 1074832 | 2/2001 |
| 2005/0003470 A1 | 1/2005 | Nelson ......................... 435/14 | EP | 1093854 | 4/2001 |
| 2005/0004494 A1 | 1/2005 | Perez ....................... 600/583 | EP | 1 101 443 | 5/2001 |
| 2005/0008537 A1 | 1/2005 | Mosolu ...................... 422/56 | EP | 1114995 | 7/2001 |
| 2005/0008851 A1 | 1/2005 | Ezoe ....................... 428/336 | EP | 0736607 | 8/2001 |
| 2005/0009191 A1 | 1/2005 | Swenson .................... 436/43 | EP | 0730037 | 12/2001 |
| 2005/0010090 A1 | 1/2005 | Acosta ..................... 600/316 | EP | 0636879 | 1/2002 |
| 2005/0010093 A1 | 1/2005 | Ford ......................... 600/345 | EP | 0851224 | 3/2002 |
| 2005/0010134 A1 | 1/2005 | Douglas ................... 600/573 | EP | 0856586 | 5/2002 |
| 2005/0010137 A1 | 1/2005 | Hodges .................... 600/583 | EP | 0817809 | 7/2002 |
| 2005/0010198 A1 | 1/2005 | Marchitto .................... 606/9 | EP | 0872728 | 7/2002 |
| 2005/0011759 A1 | 1/2005 | Moerman ............... 204/403.03 | EP | 0795748 | 8/2002 |
| 2005/0013731 A1 | 1/2005 | Burke .......................... 422/56 | EP | 0685737 | 9/2002 |
| 2005/0014997 A1 | 1/2005 | Ruchti ....................... 600/310 | EP | 0880692 | 1/2004 |
| 2005/0015020 A1 | 1/2005 | Levaughn ................. 600/583 | EP | 1246688 | 5/2004 |
| 2005/0016844 A1 | 1/2005 | Burke ..................... 204/403.1 | EP | 1790288 A1 | 5/2007 |
| 2005/0019212 A1 | 1/2005 | Bhullar ....................... 422/56 | EP | 2039294 A1 | 3/2009 |
| 2005/0019219 A1 | 1/2005 | Oshiman ................. 422/82.12 | FR | 2 555 432 A | 5/1985 |
| 2005/0019805 A1 | 1/2005 | Groll ............................ 435/6 | GB | 2168815 | 6/1986 |
| 2005/0019945 A1 | 1/2005 | Groll ......................... 436/169 | GB | 233936 A | 6/1999 |
| 2005/0019953 A1 | 1/2005 | Groll ......................... 436/514 | GB | 2335860 A | 10/1999 |
| 2005/0021066 A1 | 1/2005 | Kuhr ......................... 606/181 | GB | 2335990 A | 10/1999 |
| 2005/0027181 A1 | 2/2005 | Goode et al. | JP | 2-326247 | 11/1990 |
| 2006/0100542 A9 | 5/2006 | Wong et al. | JP | 10-296325 | 10/1998 |
| 2007/0142748 A1 | 6/2007 | Deshmukh et al. | WO | WO 80/01389 | 7/1980 |
| 2007/0173741 A1 | 7/2007 | Deshmukh et al. | WO | WO 85/04089 | 9/1985 |
| 2008/0047764 A1 | 2/2008 | Lee et al. | WO | WO 86/07632 | 12/1985 |
| 2008/0194987 A1 | 8/2008 | Boecker | WO | WO 91/09139 | 6/1991 |
| | | | WO | WO 93/06979 | 4/1993 |
| | FOREIGN PATENT DOCUMENTS | | WO | WO 93/25898 | 12/1993 |
| | | | WO | WO 94/27140 | 11/1994 |
| DE | 10032042 | 1/2002 | WO | WO 94/29703 | 12/1994 |
| DE | 10057832 | 2/2002 | WO | WO 94/29704 | 12/1994 |
| DE | 10142232 | 3/2003 | WO | WO 94/29731 | 12/1994 |
| EP | 0199484 A2 | 10/1986 | WO | WO 95/00662 | 1/1995 |
| EP | 0289 269 | 11/1988 | WO | WO 95/06240 | 3/1995 |
| EP | 0320109 | 6/1989 | WO | WO 95/10223 | 4/1995 |
| EP | 0 364 208 A1 | 4/1990 | WO | WO 95/22597 | 8/1995 |
| EP | 0170375 | 5/1990 | WO | WO 96/30431 | 10/1996 |
| EP | 0136362 | 12/1990 | WO | WO 97/02359 | 1/1997 |
| EP | 0453283 | 10/1991 | WO | WO 97/02487 | 1/1997 |

| | | | | | | |
|---|---|---|---|---|---|---|
| WO | WO 97/11883 A1 | 4/1997 | | WO | WO 01/73395 | 10/2001 |
| WO | WO 97/18464 | 5/1997 | | WO | WO 01/89691 | 11/2001 |
| WO | WO 97/30344 | 8/1997 | | WO | WO 02/00101 | 1/2002 |
| WO | WO 97/42882 | 11/1997 | | WO | WO 02/02796 | 1/2002 |
| WO | WO 97/42888 | 11/1997 | | WO | WO 02/08750 | 1/2002 |
| WO | WO 97/45720 | 12/1997 | | WO | WO 02/08753 | 1/2002 |
| WO | WO 98/03431 | 1/1998 | | WO | WO 02/08950 | 1/2002 |
| WO | WO 98/19159 | 5/1998 | | WO | WO 02/18940 | 3/2002 |
| WO | WO 98/20332 | 5/1998 | | WO | WO 02/32559 | 4/2002 |
| WO | WO 98/20348 | 5/1998 | | WO | WO 02/41779 | 5/2002 |
| WO | WO 98/24366 | 6/1998 | | WO | WO 02/44948 | 6/2002 |
| WO | WO 98/24373 | 6/1998 | | WO | WO 02/056769 A1 | 7/2002 |
| WO | WO 98/35225 | 8/1998 | | WO | WO 02/059734 | 8/2002 |
| WO | WO 99/03584 | 1/1999 | | WO | WO 02/069791 | 9/2002 |
| WO | WO 99/05966 | 2/1999 | | WO | WO 02/077638 | 10/2002 |
| WO | WO 99/07431 A1 | 2/1999 | | WO | WO 02/100251 | 12/2002 |
| WO | WO 99/13100 | 3/1999 | | WO | WO 02/100252 | 12/2002 |
| WO | WO 99/19507 | 4/1999 | | WO | WO 02/100253 | 12/2002 |
| WO | WO 99/19717 | 4/1999 | | WO | WO 02/100254 | 12/2002 |
| WO | WO 99/27852 | 6/1999 | | WO | WO 02/100460 | 12/2002 |
| WO | WO 99/62576 | 12/1999 | | WO | WO 02/100461 | 12/2002 |
| WO | WO 99/64580 | 12/1999 | | WO | WO 02/101343 | 12/2002 |
| WO | WO 00/09184 | 2/2000 | | WO | WO 02/101359 | 12/2002 |
| WO | WO 00/30186 | 5/2000 | | WO | WO 03/000321 | 1/2003 |
| WO | WO 00/39914 | 7/2000 | | WO | WO 03/023389 | 3/2003 |
| WO | WO 00/44084 | 7/2000 | | WO | WO 03/042691 | 5/2003 |
| WO | WO 00/50771 | 8/2000 | | WO | WO 03/045557 | 6/2003 |
| WO | WO 00/60340 | 10/2000 | | WO | WO 03/046542 | 6/2003 |
| WO | WO 00/64022 | 10/2000 | | WO | WO 03/049609 | 6/2003 |
| WO | WO 00/67245 | 11/2000 | | WO | WO 03/050534 | 6/2003 |
| WO | WO 00/67268 | 11/2000 | | WO | WO 03/066128 | 8/2003 |
| WO | WO 01/00090 | 1/2001 | | WO | WO 03/070099 | 8/2003 |
| WO | WO 01/00090 A1 | 1/2001 | | WO | WO 03/071940 | 9/2003 |
| WO | WO 01/15807 | 3/2001 | | WO | WO 03/082091 A2 | 10/2003 |
| WO | WO 01/16578 A1 | 3/2001 | | WO | WO 03/088851 A1 | 10/2003 |
| WO | WO 01/75433 | 3/2001 | | WO | WO 2004/008130 | 1/2004 |
| WO | WO 01/23885 | 4/2001 | | WO | WO 2004/026130 | 4/2004 |
| WO | WO 01/25775 | 4/2001 | | WO | WO 2004/041082 | 5/2004 |
| WO | WO 01/26813 | 4/2001 | | WO | WO 2004/054455 | 7/2004 |
| WO | WO 01/33216 | 5/2001 | | WO | WO 2004/060174 | 7/2004 |
| WO | WO 01/34029 | 5/2001 | | WO | WO 2004/060446 | 7/2004 |
| WO | WO 01/36955 | 5/2001 | | WO | WO 2004/091693 | 10/2004 |
| WO | WO 01/45014 A1 | 6/2001 | | WO | WO 2004/107964 | 12/2004 |
| WO | WO 01/40788 | 7/2001 | | WO | WO 2004/107975 | 12/2004 |
| WO | WO 01/57510 | 8/2001 | | WO | WO 2004/112602 | 12/2004 |
| WO | WO 01/64105 | 9/2001 | | WO | WO 2004/112612 A1 | 12/2004 |
| WO | WO 01/66010 | 9/2001 | | WO | WO 2005/001418 | 1/2005 |
| WO | WO 01/66010 A1 | 9/2001 | | WO | WO 2005/104948 A1 | 11/2005 |
| WO | WO 01/72220 A | 10/2001 | | WO | WO 2005/120365 A1 | 12/2005 |
| WO | WO 01/72225 | 10/2001 | | | | |
| WO | WO 01/73124 | 10/2001 | | \* cited by examiner | | |

METHOD AND APPARATUS FOR LANCET LAUNCHING DEVICE INTERGRATED ONTO A BLOOD-SAMPLING CARTRIDGE

TECHNICAL FIELD

Lancing devices are well known in the medical health-care products industry for piercing the skin to produce blood for analysis. Biochemical analysis of blood samples is a diagnostic tool for determining clinical information. Many point-of-care tests are performed using capillary whole blood, the most common being monitoring blood glucose level in diabetics. Typically, a drop of blood is obtained by making a small incision in the fingertip, creating a small wound, which generates a small blood droplet on the surface of the skin.

BACKGROUND ART

Early methods of lancing included piercing or slicing the skin with a needle or razor. Current methods utilize lancet drivers that contain a multitude of spring, cam and mass actuators to drive the lancet. These include cantilever springs, diaphragms, coil springs, as well as gravity plumbs to actuate the lancet. Typically, the device is pre-cocked, or the user cocks the device. The device is held against the skin and the user mechanically triggers the ballistic launch of the lancet.

The problem with current devices is that they require two hands to operate, one to hold the device and push a button which activates the device, and the other hand to provide a finger for lacing. After, lancing, the finger needs to be free to move to another device for collection of the blood droplet and subsequent analysis.

Generally, known methods of blood sampling require several steps. First, a measurement session is set up by gathering various paraphernalia such as lancets, launchers, test strips, instrument, etc. Second, the patient must assemble the paraphernalia by loading a sterile lancet, loading a test strip, and arming the launcher. Third, the patient must place their finger against the lancet launcher and using the other hand activate the launcher. Fourth, the patient must put down the launcher and place the bleeding finger against a test strip, which may or may not have been loaded into the instrument. The patient must insure blood has been loaded onto the test strip and the instrument has been calibrated prior to such loading. Finally, the patient must dispose of all the blood contaminated paraphernalia including the lancet. What has been needed is a blood sampling device and method that simplifies the blood sampling procedure.

DISCLOSURE OF INVENTION

Embodiments of the present invention are related to medical health-care products and to methods for obtaining blood for chemical analysis. More particularly, embodiments of the invention relate to devices and methods for piercing the skin (lancing) with a sensor to detect the presence of a patient's finger and activate the lancet automatically. In some embodiments, the cartridge and lancet are disposable.

In accordance with embodiments of the invention, a patient will be able to obtain a sample of blood in an ergonomic, convenient way using a method and apparatus which integrates lancing, sample collection, and analysis. The presence of patients finger on the ergonomic sampling area is sensed by monitoring the pressure applied by the finger on the cartridge which houses the lancet. The application of a predetermined pressure is measured by a piezoelectric or electrical circuit.

Advantages can be achieved in a blood sampling device by integrating the lancing and blood sample collection procedure so that the device can capture and transport the capillary blood from the wound created by the lancet to a desired active area, such as a strip for analyzing glucose. This can be done in embodiments of the invention by integrating the lancet, conduit and reservoir into a disposable cartridge which can be inserted into a hand-held sampling device with instrumentation for analyzing the blood sample.

In the use of an embodiment of the invention, a finger is placed over an ergonomically contoured sampling area and pressure is applied with the finger so that a sensor will activate the lancet, which will, in turn, lance the finger and allow the blood sample to be collected in the conduit and transported to the reservoir for analysis in a single step from the patient's perspective.

BRIEF DESCRIPTION OF DRAWING

The objects, advantages and features of this invention will be more readily appreciated from the following detailed description, when read in conjunction with the accompanying drawing, in which.

BEST MODE FOR CARRYING OUT THE INVENTION

Reference will now be made to embodiments of the invention, examples of which are illustrated in the accompanying drawings. Wherever possible, the same reference numbers will be used throughout the drawings to refer to the same or like parts.

Figure 1:
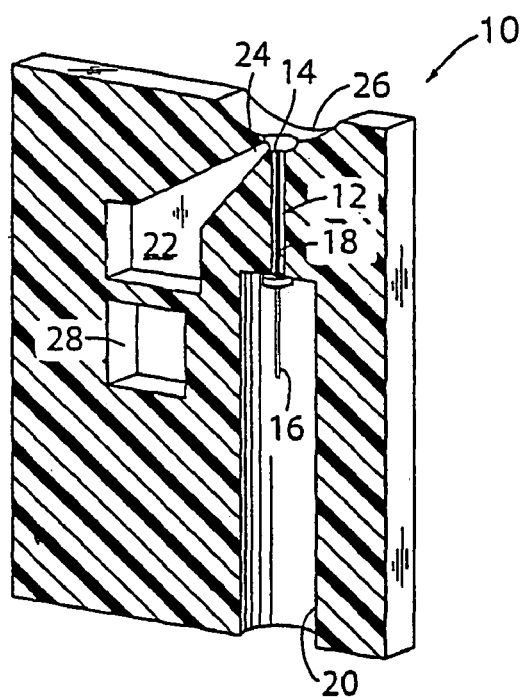
FIG. 1 is a drawing of the cartridge which houses the lancet.

FIG. 1 shows the disposable cartridge (10) which houses the lancet (12). Disposable means that the cartridge is used for one lancing cycle and is then discarded. The lancet (12) has a distal end (16) which connects to the driver (40) and a proximal end (14) which lances the skin. The proximal end (14) is embedded within the conduit (18). Embedded means completely shielded by the cartridge when it is not lancing. The distal end (16) extends, into the cavity (20). The reservoir (22) has a narrow opening (24) on the ergonomically contoured surface (26) which is adjacent to the proximal end (14) of the lancet (12). The term ergonomically contoured is generally defined to mean shaped to snugly fit a finger placed on the surface. The term reservoir is generally defined to mean an area which allows pooling of the blood sample. The term narrow is generally defined to mean a reduction in diameter of the reservoir so as to exploit capillary forces to better channel the blood into the rest of the reservoir. The term adjacent, as used in the context of the proximity of the proximal end (16) and narrow opening (24), is generally defined to mean that the proximal end (16) and the narrow opening (24) are located in the same general area. The cartridge (10) is capable of channeling the blood sample, which means transporting through small passages (not shown), to an active area (28) which corresponds to the device's system for analyzing the blood. This system can consist of a chemical, physical, optical, electrical or other means of analyzing the blood sample. The lancet and reservoir embodiment illustrated are integrated into the cartridge in a single packaged unit.

Figure 2:
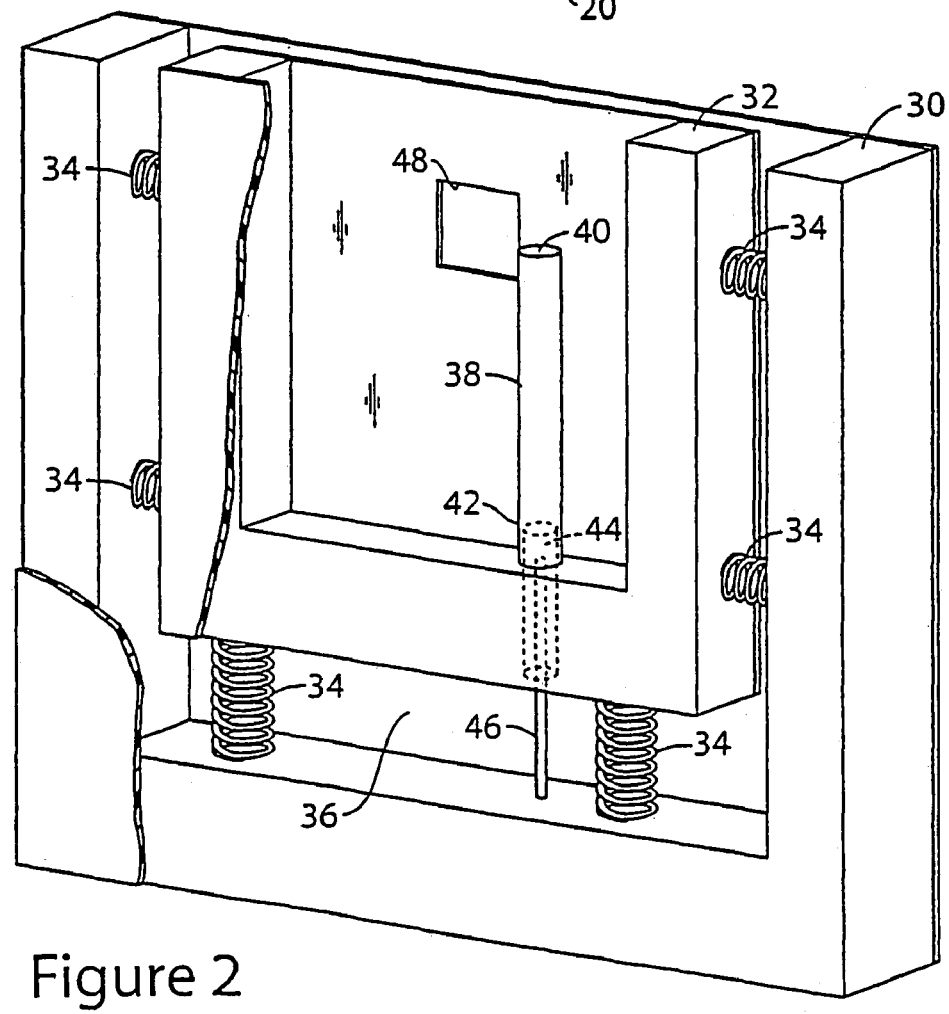
FIG. 2 is a drawing of the chamber in the sampling device where the cartridge is loaded.

FIG. 2 shows the chamber (30) in the sampling device where the cartridge is loaded. The cartridge is loaded on a socket (32) suspended with springs (34) and sits in slot (36). The launcher (38) is attached to the socket (32). The launcher has a proximal end (40) and a distal end (42). The launcher is any mechanical (such as spring or cam driven) or electrical (such as electromagnetically or electronically driven) means for advancing, stopping, and retracting the lancet. There is a clearance (44) between the distal end of the launcher (42) and the sensor (46) which is attached to the chamber (30). The socket (32) also contains the system for analyzing the blood (48) which corresponds to the active area (28) on the cartridge (10) when it is loaded into the socket (32).

Figure 3:
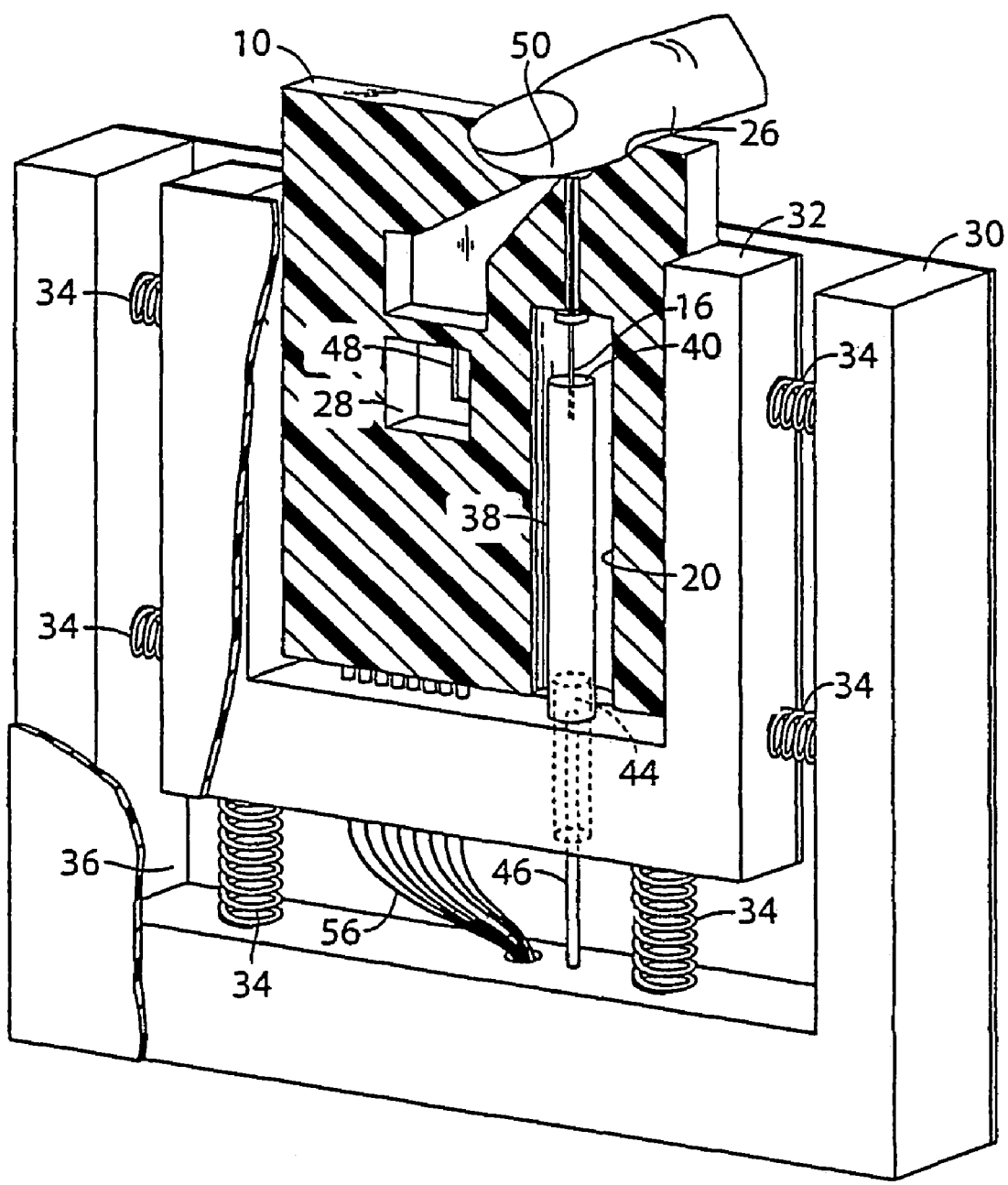
FIG. 3 is a drawing of the cartridge loaded into the sampling device.

FIG. 3 shows a cartridge (10) loaded into the socket (32). The active area (28) and system for analyzing the blood (48) overlap. The launcher (38) fits into the cavity (20). The proximal end (40) of the launcher (38) abuts the distal end (16) of the lancet (12). The patient's finger (50) sits on the ergonomically contoured surface (26).

Figure 4:
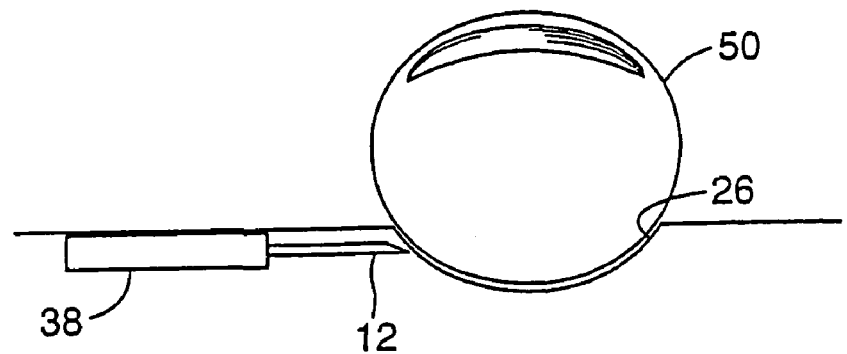
FIG. 4 is a drawing of an alternate lancet configuration.

FIG. 4 shows a drawing of an alternate lancet configuration where the lancet (12) and launcher (38) are oriented to lance the side of the finger (50) as it sits on the ergonomically contoured surface (26).

Figure 5:
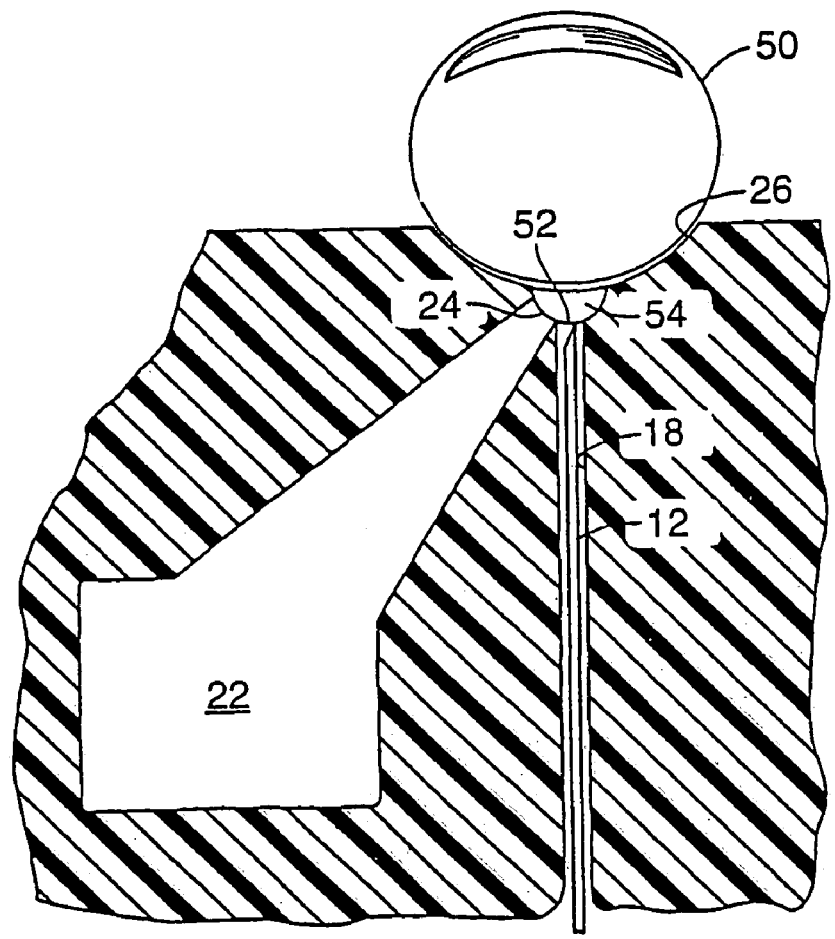
FIG. 5 is a drawing of the orifice and ergonomically contoured sampling area.

FIG. 5 illustrates with exploded detail the orifice (52) and ergonomically contoured surface (26). The conduit (18) has an orifice (52) which opens on a blood well (54). The narrow opening (24) of the reservoir (22) also opens on the blood well (54). The diameter of the narrow opening (24) is significantly greater than the diameter of the orifice (52) which is substantially the same diameter as the diameter of the lancet (12). After the lancet is retracted, the blood flowing from the finger (50) will collect in the blood well (54). The lancet (12) will have been retracted into the orifice (52) effectively blocking the passage of blood down the orifice (52). The blood will flow from the blood well (54) through the narrow opening (24) into the reservoir (22).

Figure 6:
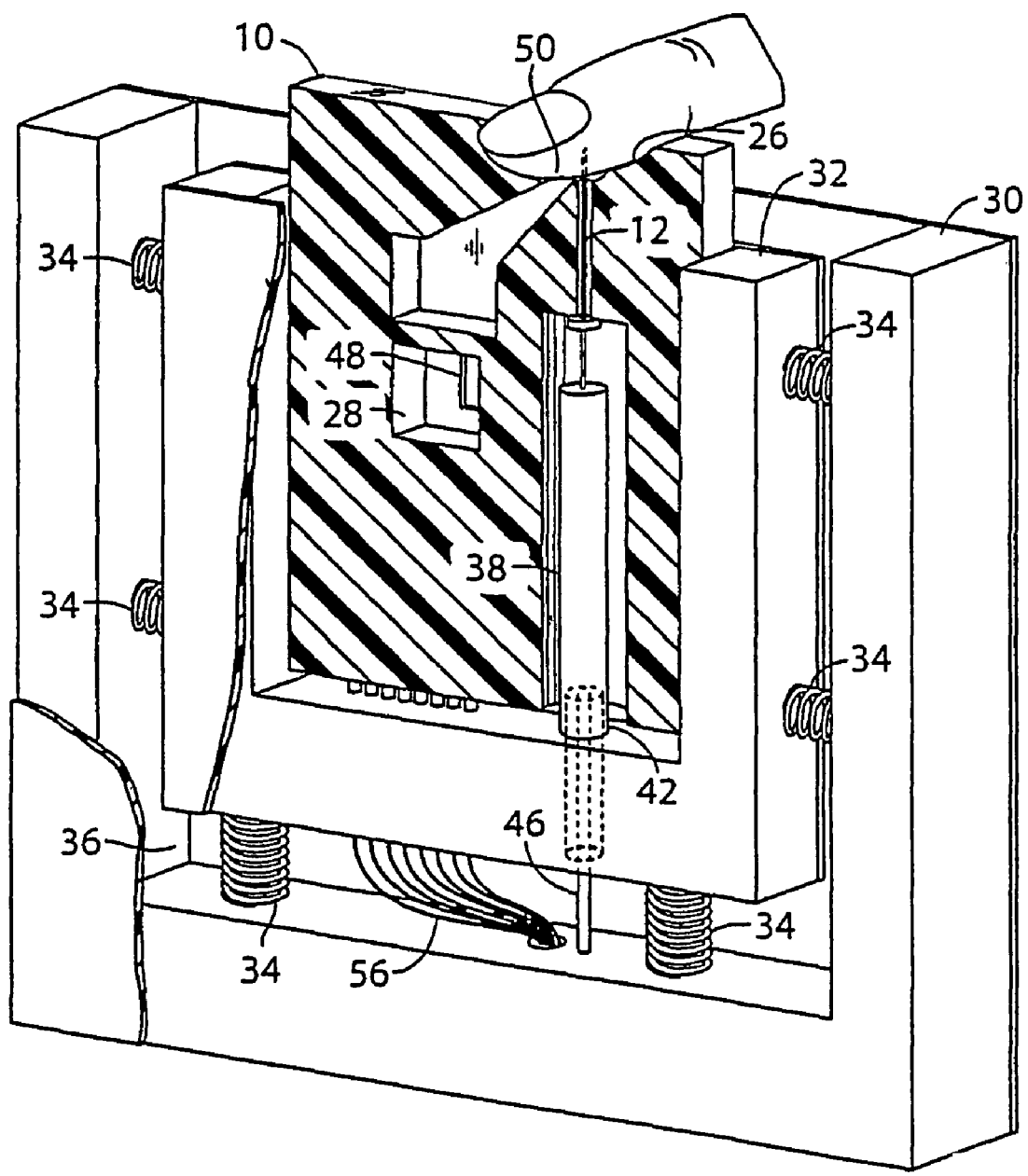
FIG. 6 is a drawing of the lancing event.

FIG. 6 shows a drawing of the lancing event. The patient applies pressure by pushing down with the finger (50) on the ergonomically contoured surface (26). This applies downward pressure on the cartridge (10) which is loaded into the socket (32). As the socket (32) is pushed downward it compresses the springs (34). The sensor (46) makes contact with the distal end (42) of the launcher (38) and thereby detects the presence of the finger on the ergonomically contoured surface. Detection means sensing using electrical means. The sensor is a piezoelectric device which detects this pressure and sends a signal to circuit (56) which actuates the launcher (38) and advances and then retracts the lancet (12) lancing the finger (50). In another embodiment, the sensor (46) is an electric contact which closes a circuit when it contacts the launcher (38) activating the launcher (38) to advance and retract the lancet (12) lancing the finger (50). Activating means beginning the lancing event, which consists of advancing, stopping, and retracting the lancet.

An embodiment of the invention is a method of sampling which reduces the number of steps that must be taken by a patient to obtain a sample and analysis of the sample. First, the patient loads a cartridge with an embedded sterile lancet into the device. Second, the patient initiates a lancing cycle by turning on the power to the device or by placing the finger to be lanced on the ergonomically contoured surface and pressing down. Initiation means arming the device. This initiation prompts the sensor. Prompting means that the sensor is made operational and given control to activate the launcher. Prompting is a safety precaution to avoid unintentionally launching the lancet. The sensor is unprompted when the lancet is retracted after its lancing cycle to avoid multiple lancing events that would cause unnecessary pain and obstruct the collection of the blood sample. The lancing cycle consists of arming, advancing, stopping and retracting the lancet, and collecting the blood sample in the reservoir. The cycle is complete once the blood sample has been collected in the reservoir. Third, the patient presses down on the cartridge which forces the launcher to make contact with the sensor and activates the launcher. The lancet then pierces the skin and the reservoir collects the blood sample. The patient is then optionally informed to remove the finger by an audible signal such as a buzzer or a beeper, and/or a visual signal such as an LED or a display screen. The patient can then dispose of all the contaminated parts by removing the cartridge and disposing of it. In another embodiment, multiple cartridges may be loaded into the sampling device in the form of a cassette. The patient is informed by the device as to when to dispose of the entire cassette after the analysis is complete.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A sampling device comprising:
   a lancet for obtaining a blood sample from a user, said lancet having a distal end and a proximal end;
   a reservoir for collecting the blood sample adjacent to the distal end of said lancet;
   an electrically-driven launcher adapted to actuate said lancet;
   a skin presence sensor coupled to circuitry, the skin presence sensor detecting presence of said user skin and in response the circuitry sends a signal to the launcher to activate the launcher automatically upon measuring application of a predetermined pressure by the user with the circuitry instructing the launcher to advance, dwelling and withdrawal of the lancet from a tissue site associated with the user skin, wherein the lancet, reservoir, electronic launcher, and skin presence sensor are part of the sampling device as an integrated device.

2. A sampling device according to claim 1 wherein said device further comprises:
   a system for analyzing the blood sample.

3. A sampling device according to claim 2 wherein:
   said lancet and said reservoir are integrated into a disposable cartridge.

4. A sampling device according to claim 3 wherein:
   said launcher contacts said sensor to detect said user and to activate said launcher.

5. A sampling device according to claim 4 wherein:
   said skin presence sensor is prompted when said disposable cartridge is loaded into said device.

6. A sampling device according to claim 5 wherein:
   said skin presence sensor is unprompted upon retraction of said lancet.

7. A sampling device according to claim 1 wherein:
   said skin presence sensor comprises a piezoelectric sensor for detecting pressure applied by said user on said piezoelectric sensor.

8. A sampling device according to claim 1 wherein:
   said skin presence sensor comprises an electric contact which closes a circuit when pressure is applied by said user on said sensor.

* * * * *

UNITED STATES PATENT AND TRADEMARK OFFICE
CERTIFICATE OF CORRECTION

PATENT NO. : 7,749,174 B2  Page 1 of 1
APPLICATION NO. : 10/363510
DATED : July 6, 2010
INVENTOR(S) : Alden It is certified that error appears in the above-identified patent and that said Letters Patent is hereby corrected as shown below:

Title Page, Item (54) Title: and Col. 1, Line 1 should read:

Method And Apparatus For Lancet Launching Device Integrated Onto A Blood-Sampling Cartridge Signed and Sealed this Twenty-fourth Day of August, 2010

David J. Kappos
*Director of the United States Patent and Trademark Office*